United States Patent [19]

Hansen

[11] Patent Number: 5,744,953
[45] Date of Patent: Apr. 28, 1998

[54] MAGNETIC MOTION TRACKER WITH TRANSMITTER PLACED ON TRACKED OBJECT

[75] Inventor: Per Krogh Hansen, Burlington, Vt.

[73] Assignee: Ascension Technology Corporation, Burlington, Vt.

[21] Appl. No.: 705,305

[22] Filed: Aug. 29, 1996

[51] Int. Cl.[6] .............................. G01B 7/14; G01B 7/30; G01R 33/00; A61B 5/103
[52] U.S. Cl. ...................... 324/207.17; 324/226; 128/782
[58] Field of Search .......................... 324/207.17, 207.26, 324/226; 342/450, 451, 463, 464, 465; 128/782

[56] References Cited

U.S. PATENT DOCUMENTS

4,710,708 12/1987 Rorden et al. ...................... 324/207.26

Primary Examiner—Walter E. Snow
Attorney, Agent, or Firm—H. Jay Spiegel

[57] ABSTRACT

The motion of a person is measured in real time using magnetic fields. A magnetic transmitter and a number of magnetic receivers are placed at different points on the person. The transmitter transmits magnetic fields sequentially from three orthogonal coils. The magnetic field is received at each receiver, which consists of three orthogonal coils. The computer resolves the sequential position and orientation coordinates from each receiver into the person's movement, relative to the transmitter, from knowledge of where each receiver is placed on the person. Other embodiments measure the transmitter's position and orientation relative to a fixed location outside of the person. The computer then resolves the position and orientation data into the person's motion relative to the fixed location outside of the person. A second embodiment uses pressure sensitive switches and accelerometers placed on the person's feet and a computer program to find the transmitter's position and orientation relative to a fixed starting location. A third embodiment uses an optical subsystem to find the transmitter's position and orientation relative to a fixed location. A fourth embodiment uses at least one further receiver placed in a fixed location outside of the person to find the transmitter's position and orientation relative to a fixed location. A fifth embodiment utilizes a special magnetic transmitter consisting of a one-axis long range transmitter and a two-axis short range transmitter and two further receivers placed at two fixed locations outside of the person to find the transmitter's position and orientation relative to a fixed location.

30 Claims, 9 Drawing Sheets

MAGNETIC MOTION TRACKER WITH TRANSMITTER PLACED ON TRACKED OBJECT

BACKGROUND OF THE INVENTION

The present invention relates to a Magnetic Motion Tracker System. In the present invention, multiple sensors are placed on a person, each located on different limbs or other areas. A transmitter, placed on the person, emits electromagnetic energy. The position and orientation of each sensor is measured relative to the transmitter. Pressure sensitive switches and/or accelerometers may be placed on each of the person's feet or a separate sensor may be utilized in order to relate the position and orientation measurements to data relative to a fixed coordinate system outside of the person. This data is used to reconstruct the person's actual motion in real time.

Position and orientation systems have previously been developed utilizing AC or DC magnetic fields. Each system has a severe limitation in range, since the signal amplitude decays proportional to $1/d^3$. Known DC magnetic field systems offer more compensation than the AC magnetic field systems for eddy current distortion caused by metallic objects in the environment, but severe problems still exist at distances greater than 10 feet. Systems using either AC or DC magnetic fields also require large fixed transmitting antennas.

In U.S. Pat. Nos. 4,849,692 4,945,305 both issued to Ernest B. Blood, a remote object's position and orientation are determined. The system disclosed in these patents utilizes a plurality of pulsed DC magnetic fields with long, fixed-length, steady state components. The steady state components of the generated magnetic fields are measured by DC-field sensitive sensors. The system reduces the field distortions resulting from the decay of eddy currents induced in electrically conductive materials by the generated magnetic fields. The Blood system waits a long enough time for the eddy currents to decay substantially, before measuring the steady state component of the generated magnetic fields. Blood teaches a position and orientation system in six degrees of freedom. The source is fixed and the sensor is movable. The system suffers from short operation distances, even with the use of large fixed source antennas, and problems with eddy current distortion also occur, if conductive metallic objects are present.

In U.S. Pat. No. 5,453,686 to Peter T. Anderson, a remote object's position and orientation are determined by a system utilizing a plurality of pulsed magnetic fields with long, fixed-length, steady state components. The steady state components of the generated magnetic fields are measured by passive sensors. The system reduces the field distortions resulting from the decay of eddy currents induced in electrically conductive materials by magnetic fields. The Anderson system waits a long enough time for the eddy currents to decay substantially, before measuring the steady state component of the generated magnetic fields. Anderson teaches a position and orientation system in six degrees of freedom. The source is fixed and the sensor is movable. The system suffers from short operation distances, even with the use of large source antennas, and problems with eddy current distortion also occur, if conductive metallic objects are present.

In U.S. Pat. Nos. 3,868,565; 3,983,474; 4,298,874 and 4,742,356 to Kuipers, in U.S. Pat. Nos. 4,054,881; 4,314,251, and 4,346,384 to Raab, in U.S. Pat. No. 4,328,548 to Crow et. al., in U.S. Pat. Nos. 4,287,809 and 4,393,831 to Egli et. al., in U.S. Pat. No. 4,396,885 to Constant, in U.S. Pat. No. 4,710,708 to Rorden, in U.S. Pat. No. 4,819,250 to Rotier, in U.S. Pat. Nos. 4,737,794 and 5,307,072 to Jones, and in U.S. Pat. No. 5,457,641 to Zimmer et al., Alternating Current (AC) magnetic fields are transmitted from a fixed source and are received at a movable sensor. A processor calculates the position and orientation of the sensor, relative to the fixed source, from the measurements of received magnetic fields.

All of the patents listed above, which utilize AC magnetic fields, teach a position and orientation system in various degrees of freedom. The source is fixed and the sensor is movable or vice-versa, but in none of them are both the sensor and source movable nor placed on the object whose motion is to be measured. The systems suffer from short operation distances, even when large source antennas are used and serious problems with eddy current distortion also occur, if conductive metallic objects are present.

The performance of prior art magnetic position and orientation measurement systems clearly demonstrates the need for a system that will overcome the inherent limitations with use of large source antennas over short limited range and distortion from metallic objects. The need for such a system was the impetus for the development of the present invention, a "sourceless" magnetic system, as described herein.

SUMMARY OF THE INVENTION

The present invention relates to embodiments of a magnetic motion tracker system. It is an object of the present invention to provide a unique and enhanced technique for tracking human motion in order to operate with no range limitations and with significantly enhanced cancellation or negation of eddy current distortion caused by metallic objects in the environment. According to a broad aspect of the present invention, a technique is provided of determining the motion of multiple sensors placed on a person in order to determine the person's motion in real time.

The present invention includes the following objects, aspects and features:

1) In a first embodiment, a short range magnetic field transmitter is placed on the person, preferably on the person's lower back or abdomen, which transmitter is able to transmit strong enough magnetic fields to be received by all of the receivers. The transmitted magnetic field is received by each sensor and is processed by a computer in order to find the position and orientation of each of the sensors relative to the transmitter. By placing the transmitter on the person, the maximum range of operation will be less than four feet, namely the distance from the person's lower back or abdomen down to the feet or to an outstretched hand. The following advantages result:
   A) the need for a fixed large transmitter placed away from the person is eliminated;
   B) operation at any range, without limitation, is feasible;
   C) fewer problems exist with respect to eddy current distortion due to existence of metallic objects in the environment, since the transmitter always is at close range to the receivers on the person and the metallic objects are always at farther distances from the transmitter than the receiver and most likely are only in the floor.

2) In a second embodiment, in addition to everything included in the first embodiment, pressure sensitive switches and/or accelerometers are placed on each of the feet of the person, which enables the computer to be made aware when either or both of the user's feet are on the floor, and thereby calculation of the person's motion relative to a fixed coordinate system on the floor is possible.

3) In a third embodiment, in addition to everything included in the first embodiment, an optical sensor is placed on top of the magnetic sensor on the head of the person and utilizes an optical position and orientation measurement system including a fixed optical sensor in order to measure this source's position and orientation relative to a fixed coordinate system in the room defined by the location of the fixed optical sensor. The computer calculates all of the magnetic sensors' positions and orientations relative to the fixed coordinate system, and then further calculates the person's motion relative to the fixed coordinate system.

4) In a fourth embodiment, in addition to everything included in the first embodiment, at least one fixed magnetic field receiver is placed in the measurement space. This receiver receives the magnetic field transmitted from the transmitter placed on the person. The computer calculates the transmitter's position and orientation relative to the fixed coordinate system defined by the position of the fixed magnetic field receiver and then each sensor's position and orientation relative to the fixed coordinate system.

5) In a fifth embodiment, in addition to everything included in the first embodiment, two fixed magnetic field receivers are placed in the measurement space. The three axis short range transmitter placed on the person is replaced with a one axis long range transmitter combined with a two axis short range transmitter. The receivers receive the magnetic field transmitted from the one-axis transmitter placed on the person. The computer calculates the transmitter's position and orientation relative to the fixed coordinate system and then each sensor's position and orientation relative to the fixed coordinate system.

6) The first embodiment may be described as a basic system and the second through fifth embodiments describe "accessories" to be added to the first embodiment to enhance operation and/or versatility.

Accordingly, it is a first object of the present invention to provide a magnetic motion tracker system for measuring the position and orientation of multiple sensors in six degrees of freedom.

It is a further object of the present invention to provide such a system and method that can track the motion of more than one person.

It is a still further object of the present invention to provide such a system that places a short range magnetic transmitter on each person.

It is a yet further object of the invention to provide a system that is:

1) Free of range limitations;

2) Eliminates the need for large source transmitters, and

3) Provides significantly better metallic object distortion rejection.

It is a still further object of the present invention to provide such a system in a first basic embodiment with other embodiments contemplating accessories to be added to the first embodiment.

These and other objects, aspects and features of the present invention will be better understood from the following detailed description of the preferred embodiments when read in conjunction with the appended drawing figures.

SPECIFIC DESCRIPTION OF THE PREFERRED EMBODIMENTS

Figure 1:
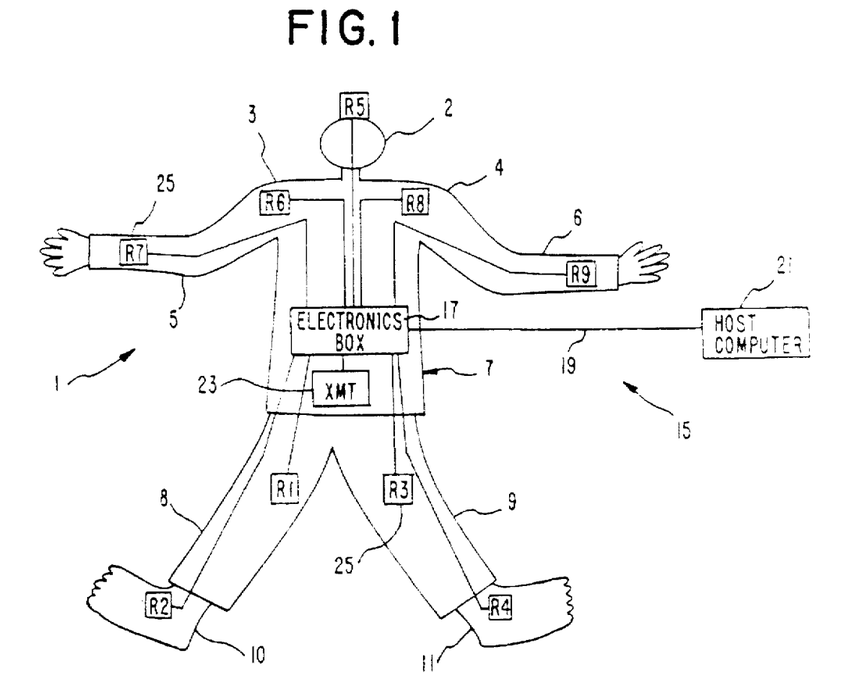
FIG. 1 shows a schematic representation of the first embodiment of the magnetic field motion tracker in accordance with the teachings of the present invention.
Figure 2:
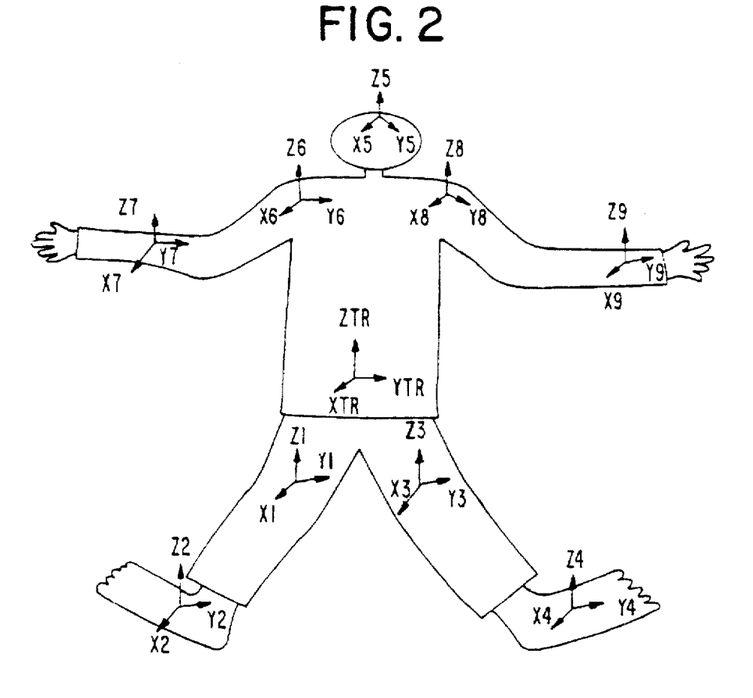
FIG. 2 shows the geometry of the first embodiment of the present invention.

With reference to FIGS. 1 and 2, a first embodiment of the present invention is depicted. For clearest understanding of the various embodiments of the present invention, in the drawing figures, a schematic representation of the body of the user is shown. The user is designated by the reference numeral 1 and includes a head 2, shoulders 3 and 4, arms 5 and 6, lower back or an abdomen 7, legs 8 and 9, and feet 10 and 11.

The first embodiment of the present invention is generally designated by the reference numeral 15 and is seen to include an electrical box 17 mounted in the middle of the lower back or abdomen 7 of the user 1 and interconnected with a host computer 21 via an electrical conductor 19. A transmitter 23 is electrically connected to the electrical box 17 and includes three orthogonal transmission coils schematically represented in the geometrical depiction of FIG. 2.

As seen in FIG. 1, a multiplicity of sensors are mounted on the body of the user 1. Each sensor is generally designated by the reference numeral 25 and the sensors are labeled R1 through R9. As seen in FIGS. 1 and 2, sensors are mounted on the head 2 of the user, at each shoulder joint 3, 4, on each arm 5, 6, adjacent the knees of the legs 8, 9, and at the ankles of the legs. As best understood from the geometrical depiction of FIG. 2, each of the sensors 25 consist of three mutually orthogonal sensor coils.

In the operation of the embodiment of FIG. 1, under the control of the microcomputer 55 (see FIGS. 13 and 14) inside the electrical box 17, the X-direction coil of the transmitter 23 is first activated and signals received at all of the mutually orthogonal coils of each sensor 25 are measured and stored in the microcomputer 55. Thereafter, under the direction of the microcomputer 55, the Y-direction coil of the transmitter 23 is activated and signals received by each of the mutually orthogonal coils of the sensors 25 are measured and stored. The system, under the direction of the microcomputer 55, then activates the Z-direction coil of the transmitter 23 and signals received by the mutually orthogonal coils of the sensors 25 are measured and stored by the microcomputer 55. The microcomputer 55 is programmed with an algorithm such as that which is employed in U.S. Pat. Nos. 4,849,692 and 4,945,305 to Blood, to find the position and orientation of each sensor 25 in six degrees of freedom with respect to the transmitter 23 and sent to the host computer 21. Thus, motions of the user 1, relative to the transmitter 23, may be measured and subsequently recreated. Examples of algorithms that may also be employed for coordinate transformation to determine motions of the user 1 include that which is known by the Trade Name "ALIAS-WAVEFRONT" or "SOFTIMAGE MOTION TRACKER SOFTWARE PACKAGES". If desired, the electrical conductor 19 may easily be replaced by a wireless data link (not shown in FIGS. 1 and 2).

Figure 3:
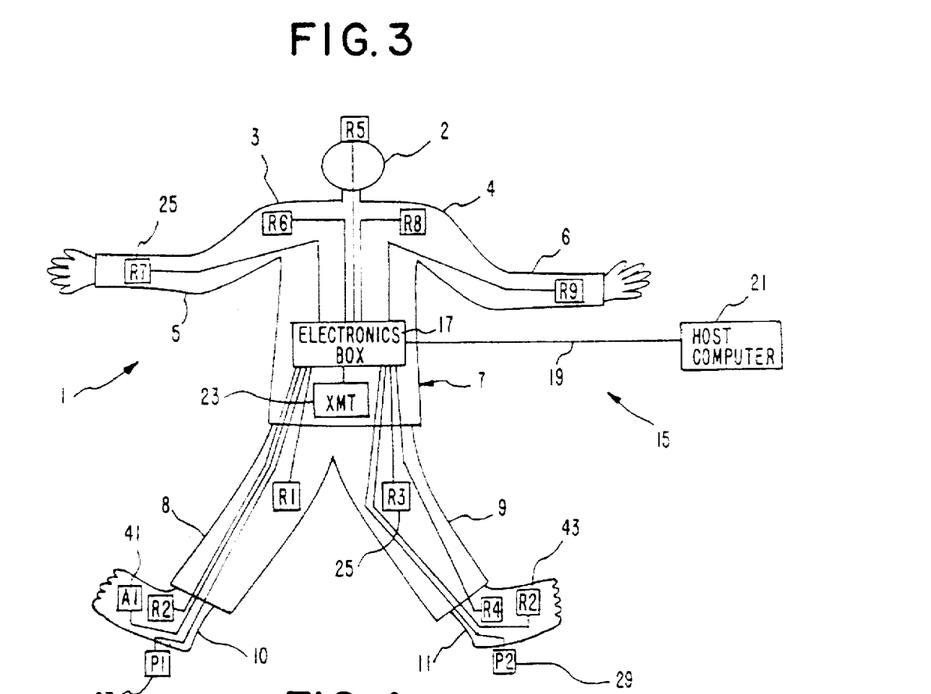
FIG. 3 shows a second embodiment of the present invention with the addition, to the first embodiment, of pressure sensitive switches and accelerometers placed on each of the user's feet.
Figure 4:
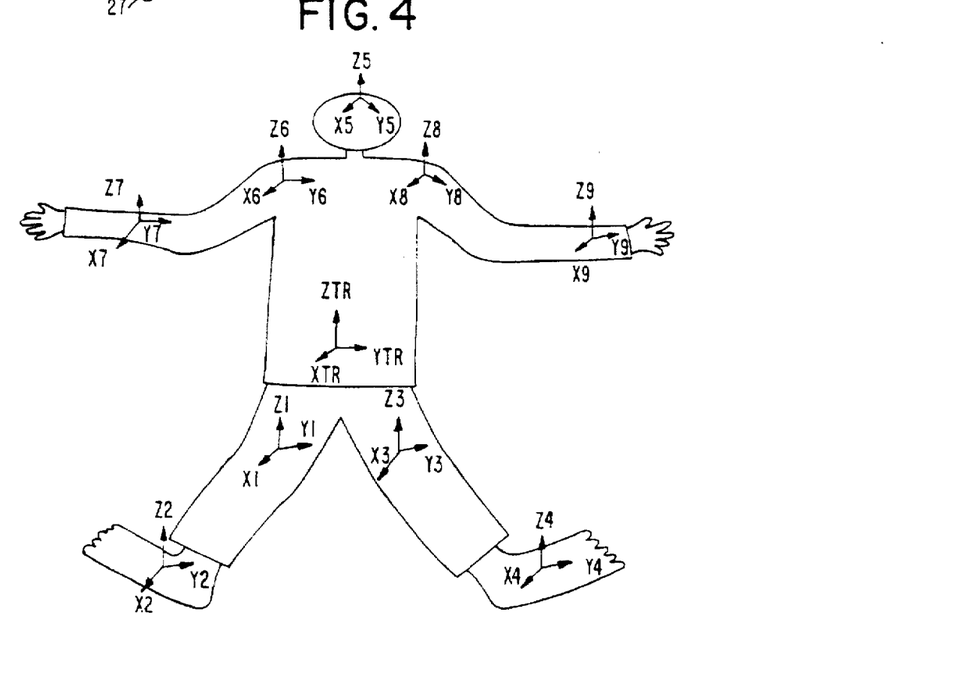
FIG. 4 shows the geometry of the second embodiment of the present invention.

FIGS. 3 and 4 show a second embodiment of the present invention. The second embodiment includes everything included in the first embodiment and, as such, the same reference numerals employed in FIGS. 1 and 2 are employed herein. The sole difference between the embodiment of FIGS. 3 and 4 and the embodiment of FIGS. 1 and 2 consists of the addition, in the embodiment of FIGS. 3 and 4, of pressure sensitive switches 27 and 29 and/or accelerometers 41 and 43, with the switch 27 and accelerometer 41 being located on the left foot 10 of the user and with the pressure sensitive switch 29 and accelerometer 43 being located on the right foot 11 of the user 1. The inventive system 15, as shown in FIGS. 3-4 with the addition of the pressure sensitive switches, operates in the same way as described with reference to FIGS. 1 and 2, in that, magnetic fields transmitted by the transmitter 23 in the X, Y and Z-direction sequentially. During such operation, the microcomputer 55 senses if one or both of the pressure sensitive switches 27, 29 are closed or open. If, for example, the pressure sensitive switch 29 located on the right foot 11 of the user 1 is closed, the host computer 21 realizes that the right foot 11 is engaging a floor surface. In the same manner, if the pressure sensitive switch 27 on the left foot 10 is closed, the host computer 21 is accordingly made aware that the left foot 10 is engaging a floor surface. When the microcomputer 55 is activated to commence measurements, both of the feet 10, 11 of the user 1 are engaging the floor surface. Thus, the microcomputer 55 records position and orientation data with respect to the transmitter 23 and translates them with respect to the location of the sensor 29 on the right foot 11 of the user 1. With reference to the geometry depicted in FIG. 4, the microcomputer 55 utilizes the position of the right foot 11 of the user 1 as a fixed reference point and as the basis for a coordinate system to be used in measurements to be taken. If the user 1 lifts his/her left foot 10, the microcomputer 55 senses that the pressure sensitive switch 27 is open, "realizes" that the left foot 10 is off the floor surface, and measures the position and orientation of every one of the nine sensors 25 (R1–R9) relative to the position of the right foot 11. When the pressure sensitive switch 27, located on the left foot 10, is closed, leading to the conclusion that the left foot 10 is on the floor, the microcomputer 55 shifts the measured position and orientation data to be with respect to the location of the left foot pressure sensitive switch 27.

Figure 5:
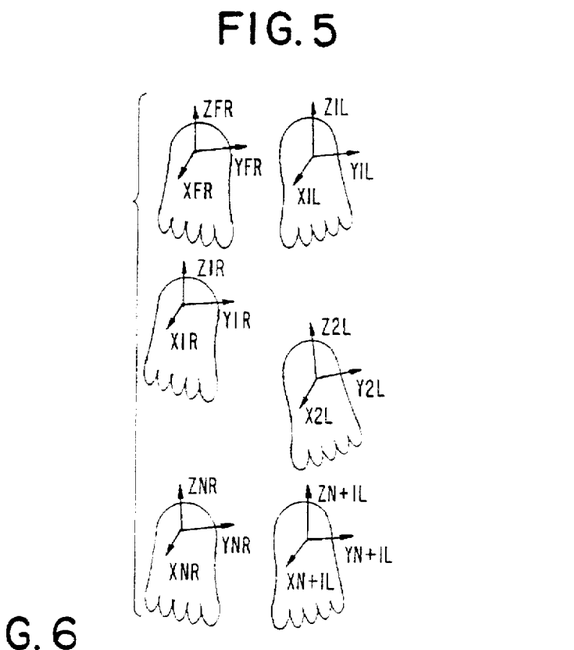
FIG. 5 shows the geometry of sequential placements of the user's feet on the floor.

FIG. 5 shows the geometry of steps taken by the user 1. Based upon beginning measurements taken when the left foot and right foot are both on the floor surface, the microcomputer 55 is aware of the position and orientation of the left foot and right foot at the beginning of a measuring sequence. When the microcomputer 55 senses that, for example, the right foot 11 has returned to the floor surface after it was off the floor surface, the host computer 21 then translates the measured data to be relative to the position and orientation of the right foot 11. The host computer 21 is aware of the position and orientation of the right foot 11 relative to the position and orientation of the left foot 10 and thereby with respect to the fixed coordinate system. The system 15 keeps track of the steps of the user 1 and always translates received data to be relative to the pressure sensitive switch that is on the foot that is still on the floor surface and then, by knowing the steps the user has taken, translates everything to be relative to the fixed reference coordinate system.

The system of FIGS. 1 and 2 with the pressure sensitive switch accessories of FIGS. 3 and 4 works effectively so long as at least one foot of the user 1 is engaging a ground surface. If the user jumps and thereby removes both feet from the ground surface, as should be understood, the system 15 will lose its reference point. It will, however, keep measuring using the last known reference point until one of the feet is again placed on the floor.

Figure 6:
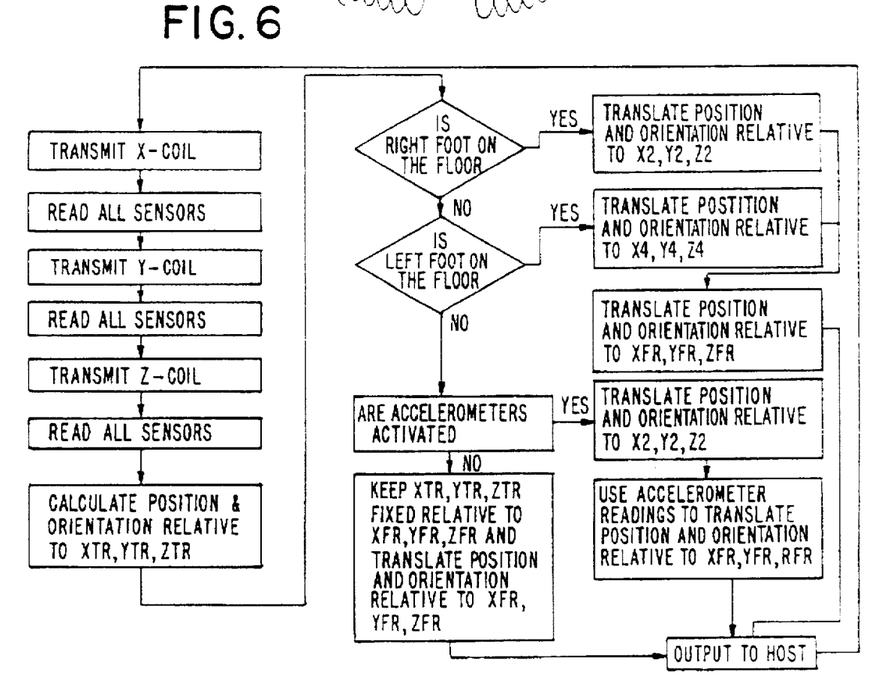
FIG. 6 shows the control algorithm for the second embodiment of the present invention.

An algorithm for the system particularly depicted in FIGS. 3 and 4 is depicted in FIG. 6. FIG. 6 is self-explanatory in light of the explanation above. The microcomputer 55 calculates the motions of the user 1, from knowledge of the placement of the sensors 25 on the user 1, relative to the fixed coordinate system defined by the first placement of the right foot 11 of the user 1 on the floor surface. In most cases, such movements will be recorded effectively even if both feet occasionally leave the floor at the same time.

The pressure switches 27 and 29 are shown as single element pressure switches. Multiple element pressure switches can be utilized for each foot. This enables the microcomputer 55 to sense if the person 1 has lifted his/her heel or toes off the floor, if the person has one element placed underneath the heel and a second element placed underneath the toes.

More accurate movements can be tracked if the person is supplied with two magnetic sensors on each foot placed above each of the pressure sensitive elements. This will allow the microcomputer 55 to determine rotations of the person's feet around either the toes or the heel.

The use of the accelerometers 41 and 43 placed on each of the person's feet will allow the microcomputer 55 to determine if the person 1 is sliding on his/her feet. It will also allow determination of the distance of the sliding motion by measuring the acceleration over a given time period. This will enable the microcomputer 55 to keep a fixed reference point, even when the person slides.

The use of the accelerometers 41 and 43 will also allow the microcomputer 55 to keep a fixed reference point even if the person 1 jumps (and thereby removes both feet from the floor at the same time), if the accelerometers 41 and 43 are three-dimensional accelerometers. The motion of a three-dimensional accelerometer can be measured for a given time period.

Figure 7:
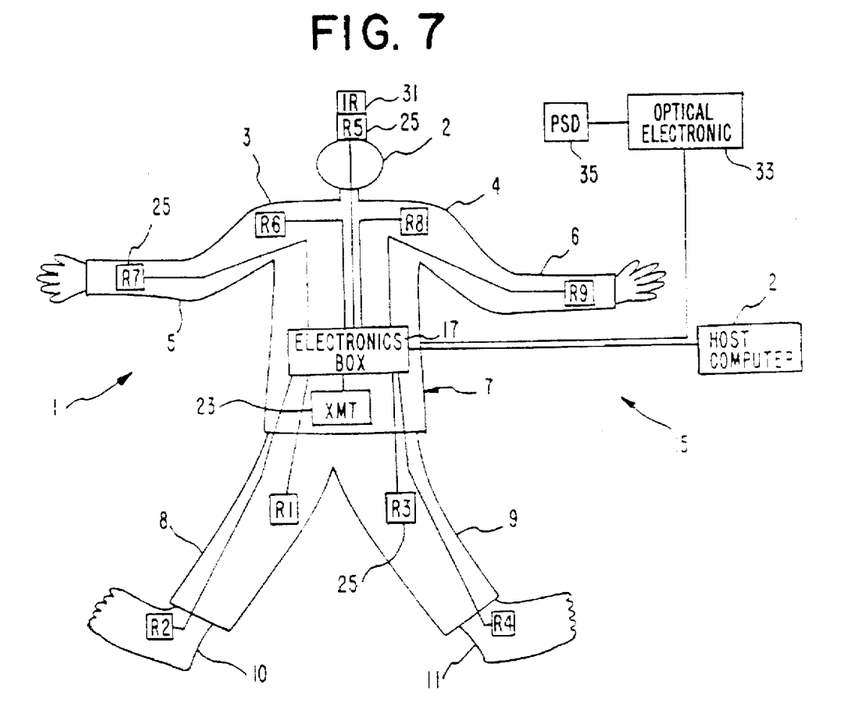
FIG. 7 shows a third embodiment of the present invention with the addition, to the first embodiment, of an infrared position and orientation system.
Figure 8:
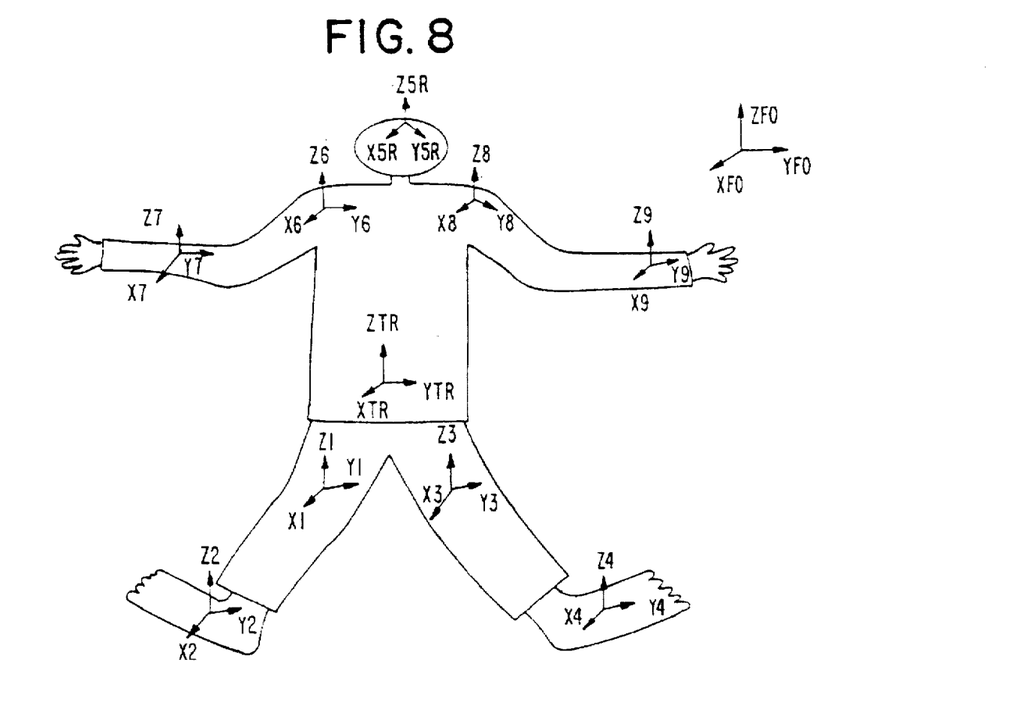
FIG. 8 shows the geometry of the third embodiment of the present invention.

FIGS. 7 and 8 show the details of a third embodiment of the present invention. The third embodiment includes all of the features and aspects of the first embodiment illustrated in FIGS. 1–2 with the further provision of the inclusion of an optical position and orientation system employing a further single source 31 mounted on the head of the user adjacent the magnetic sensor already mounted there. A base unit 33 is attached to the host computer 21 and includes a driver (not shown) comprising control means to drive a further transmitter comprising an infrared light source 31 such as, for example, an infrared light emitting diode. The source 31 transmits infrared light, which is received by the position sensing device (PSD) 35, and allows measurement of the position and orientation of the optical source 31. Since the optical source 31 and the magnetic sensor 25 located on the head 2 of the user 1 are placed together and aligned with one another, the host computer 21 can now first translate all of the position and orientation data to be with respect to the optical source 31 and then relative to the fixed coordinate system of the optical system. The microcomputer 55 then calculates the motions of the user 1 from knowledge of the placement of the sensors 25 on the user 1 relative to the fixed coordinate system defined as explained above. One example of an optical source 31 and PSD sensor 35 is that which is sold as the "OPTOCON SYSTEM" from Northern Digital. Of course, any optical position and orientation measurement system may be suitably employed.

Figure 9:
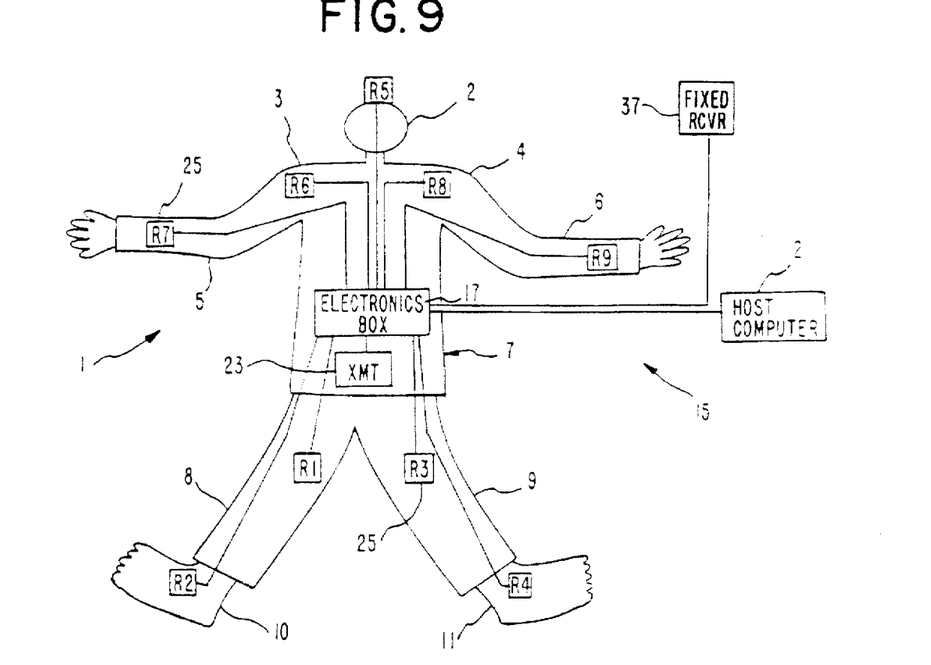
FIG. 9 shows a fourth embodiment of the present invention with the addition, to the first embodiment, of a fixed magnetic field receiver.
Figure 10:
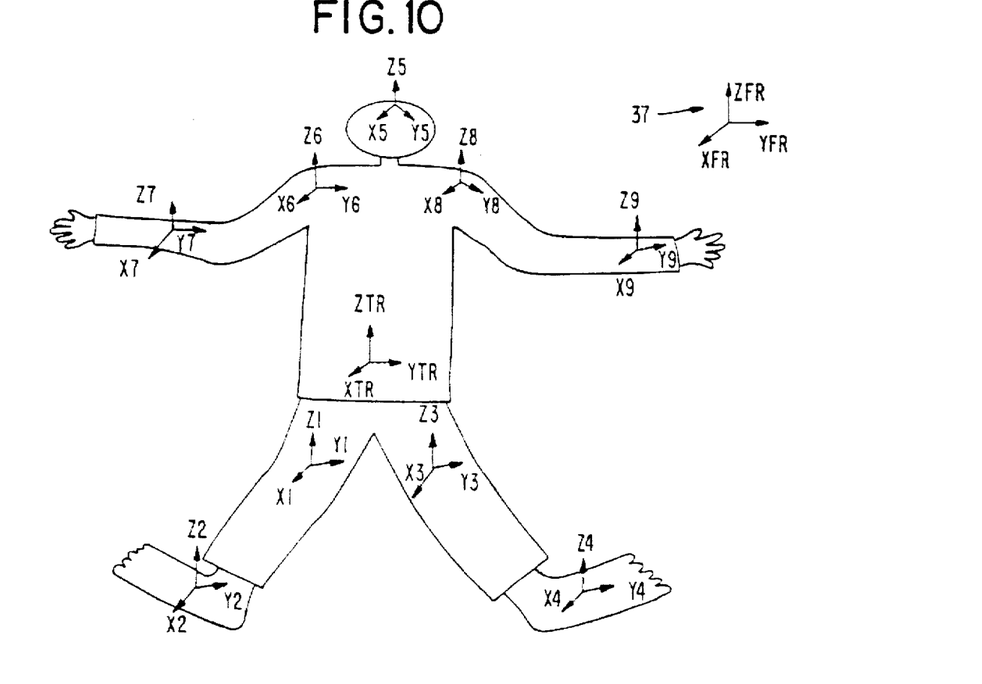
FIG. 10 shows the geometry of the fourth embodiment of the present invention.

FIGS. 9 and 10 show a fourth embodiment of the present invention. The fourth embodiment of the present invention includes each and every feature of the first embodiment of FIGS. 1 and 2 but with the further provision of a fixed magnetic receiver 37 that consists of three orthogonal coils as schematically depicted in FIG. 10. When magnetic fields are transmitted by the transmitter 23 centrally located on the body of the user 1, as these fields are sensed by the sensors 25 strategically mounted on the body of the user 1, they are also received by the three mutually orthogonal coils of the fixed receiver 37, with a schematic representation of the orthogonality of the coils being shown in FIG. 10. The microcomputer 55 utilizes measurements derived from receipt of magnetic fields by the sensor 37 to calculate the position and orientation of the transmitter 23 with respect to the fixed coordinate system defined by the receiver 37. The algorithm employed to calculate the position and orientation of the transmitter 23 may be that which is disclosed in the two patents to Blood, discussed above. With data in hand from the various components of the embodiment of FIGS. 9 and 10, motion of the user 1 may be calculated relative to the above-described fixed coordinate system defined by the location of the receiver 37. Since it is possible that measurements incorporating the location of the fixed receiver 37 may be made over far distances, data as to the position and orientation of the sensors 25 mounted on the user 1 may be less accurate than measurements made in the embodiments of FIGS. 1–8. However, such coordinates are only utilized to reference the more accurate measurements for the motions of the user 1 taken by the receivers in close range on the user 1 to a fixed point in the room. In most instances, the system illustrated in FIGS. 9 and 10 is more than adequate to capture and store motions of a user.

The further fixed receiver 37 may also be made movable so that it is always at close range to the transmitter 23 placed on the person 1, so that it will always receive a strong magnetic field and thereby always have a good signal-to-noise ratio. The receiver 37's Y and Z axis as well as its orientation are held fixed, so that only its X coordinate will vary and need to be measured in order to find its position and orientation relative to the fixed coordinate system.

It is, of course, possible to use any number of fixed magnetic receivers in order to cover any size area with sufficient S/N. The control program in the microcomputer 55 simply uses the fixed receiver with the strongest received signals as the fixed coordinate system. Since the placement of all the fixed receivers are known, it is easy to maintain only one fixed reference coordinate system.

Figure 11:
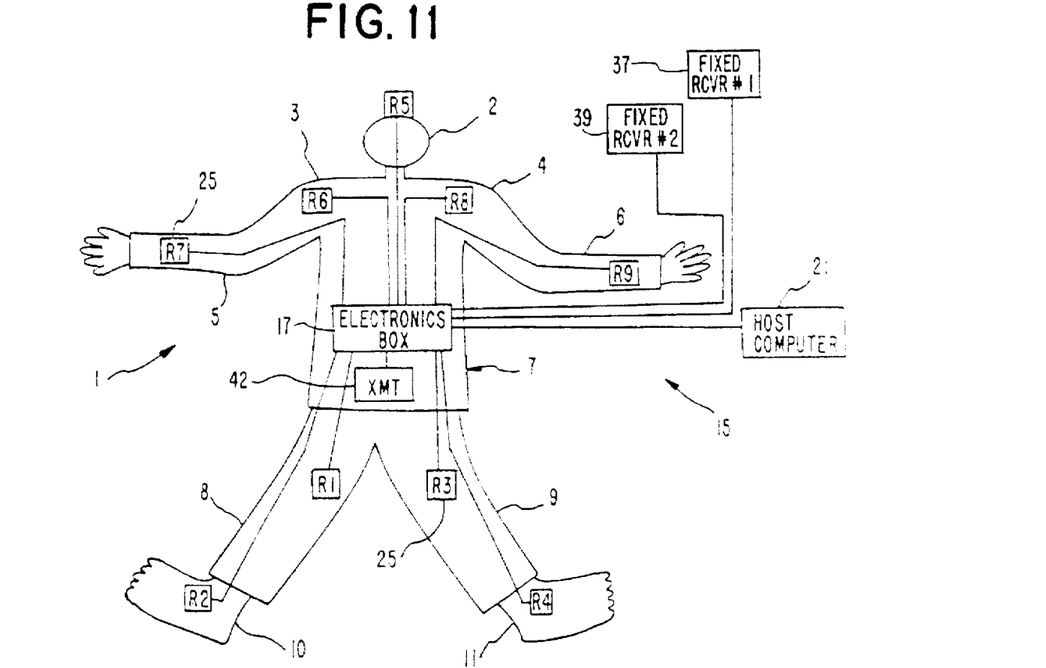
FIG. 11 shows a fifth embodiment of the present invention with the addition, to the first embodiment, of two fixed magnetic field receivers and a modified three axis transmitter (one axis long range and two axis short range).
Figure 12:
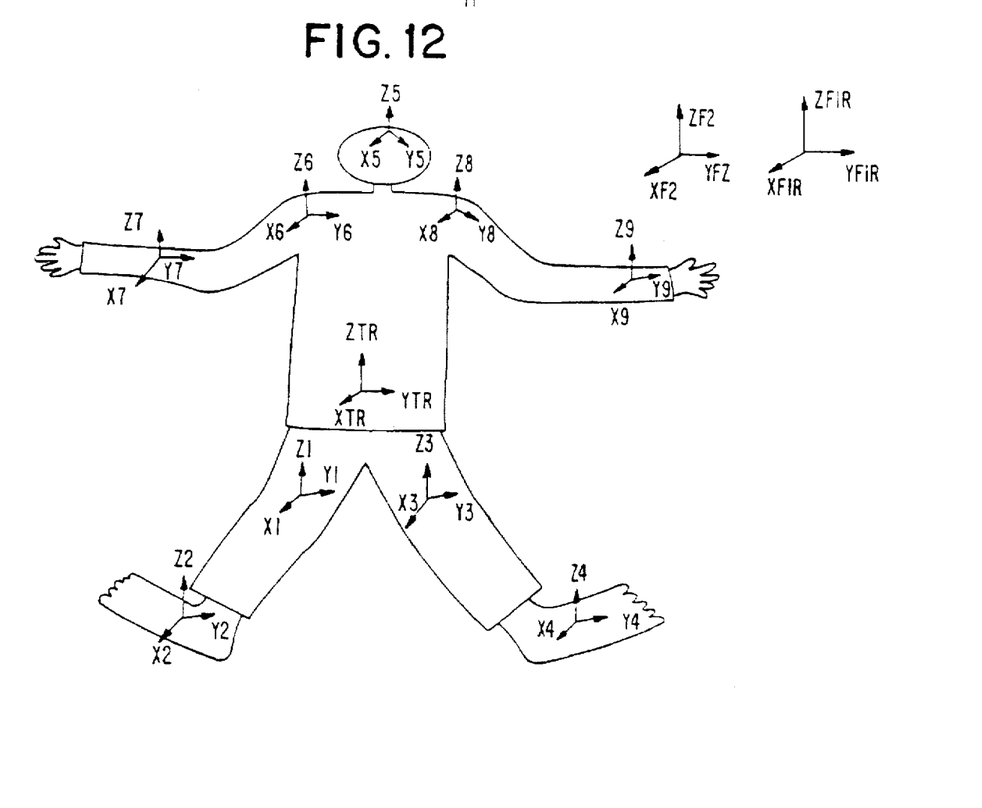
FIG. 12 shows the geometry of the fifth embodiment of the present invention.

FIGS. 11 and 12 depict a fifth embodiment of the present invention that includes all of the features and aspects of the first embodiment illustrated in FIGS. 1 and 2 but with the addition of two fixed magnetic receivers, the first one of which is labeled by the reference numeral 37 and is the same as that which is depicted in the embodiment of FIGS. 9 and 10, along with a second fixed magnetic field receiver 39 spaced from the receiver 37. Additionally, the transmitter 23 from the embodiments of FIGS. 1–10 has been replaced with a different transmitter 42 that has three mutually orthogonal transmitter coils, one of which is a long range transmitter coil and the others of which are short range transmitter coils. When the long range transmitter coil is activated, the fixed receivers 37 and 39 measure the received magnetic field and calculate the position and orientation of the one axis transmitter with respect to a fixed coordinate system defined by the fixed receivers 37, 39. If desired, the algorithm employed in such calculations could be as disclosed in U.S. Pat. No. 4,710,708 to Rorden. However, such algorithm will not permit calculation of the roll angle around the axis of the one-axis transmitter. This problem can be solved by activating, at every other activation of the one-axis transmitter, another one of the transmitter coils utilizing a DC or AC current. Such activation will act to turn the generated magnetic field and, by comparing the two outputs, the roll angle can be determined. The host computer 21 utilizes these measurements to calculate the position and orientation of the transmitter 42 with respect to the fixed coordinate system defined by the receivers 37 and 39.

The geometry of the system of FIGS. 11 and 12 is depicted in FIG. 12. In the embodiment of FIGS. 11 and 12, since measurements are made over relatively far distances as compared to the distances in the embodiments of FIGS. 1–8, with the use of a long range transmitter, as described above, position and orientation data will be more accurate than the accuracy of the data derived from practicing the embodiment of FIGS. 9 and 10. The fixed coordinate system defined by the receivers 37 and 39 is only utilized to reference the more accurate measurements for motion taken by the sensors R1–R9 mounted on the user 1, with respect to a fixed point in the space.

Figure 13:
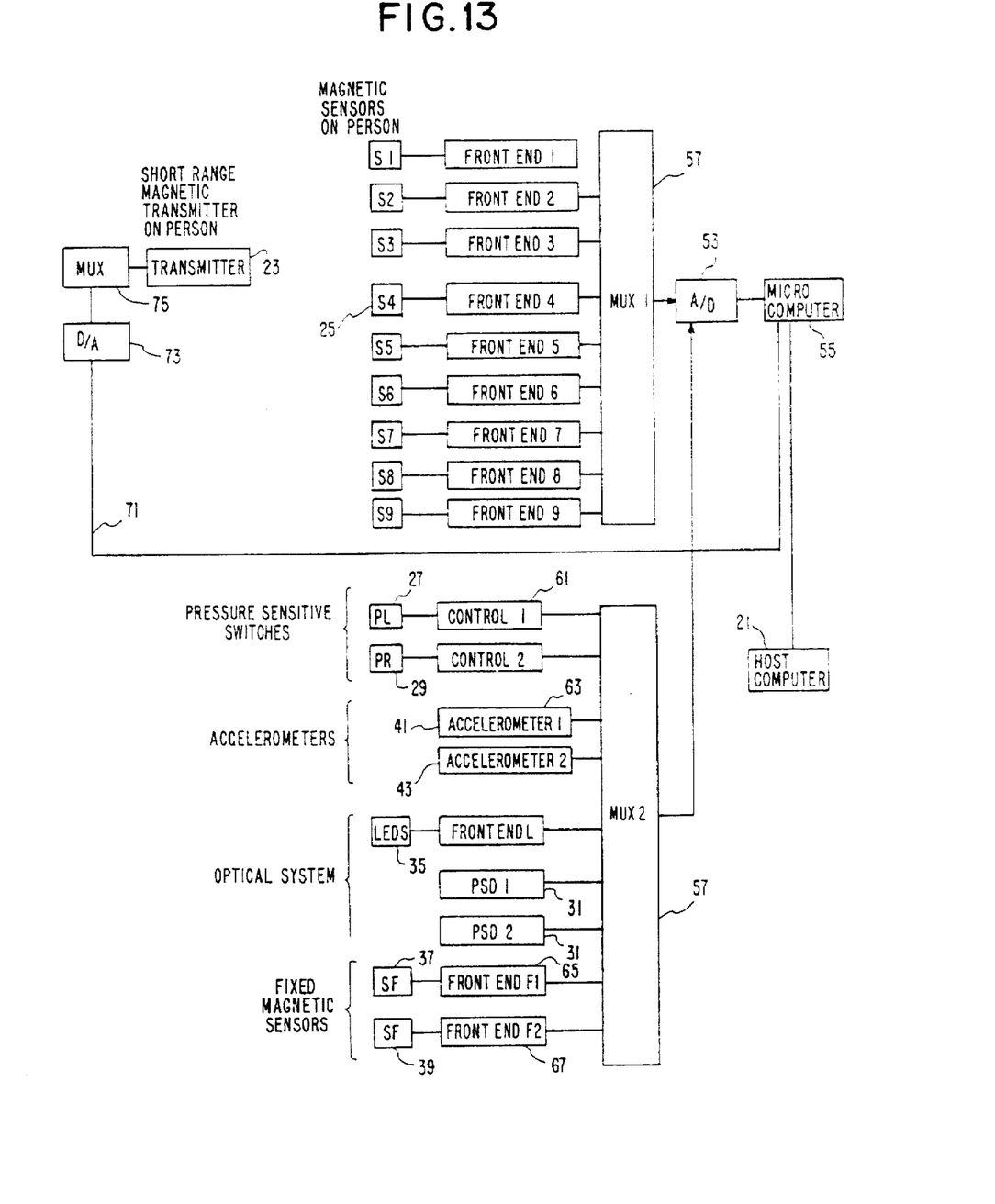
FIG. 13 shows a block diagram of all of the five embodiments of the present invention combined together.

FIG. 13 depicts a system consisting of the combination of all of the embodiments illustrated in FIGS. 1–12. In particular, FIG. 13 provides a detailed depiction of the fact that the embodiments of FIGS. 3–12 are, in fact, the depiction of various accessories to be added on to the system of FIGS. 1–2.

FIG. 13 shows certain features not shown in FIGS. 1–12 including the multiplexer 51 that receives signals from the sensors 25 and sequentially provides them via the A/D converter 53 to the microcomputer 55. A further multiplexer 57 receives signals from the various accessories and sequentially supplies those signals via the A/D converter 53 to the microcomputer 55. These accessories include the pressure sensitive switches 27, 29, as particularly described with reference to FIGS. 3-4, the optical system light source 35 and receiver 31 as particularly shown with reference to FIGS. 7-8, the fixed magnetic sensor 37 best seen with reference to FIGS. 9 and 10, and the dual magnetic sensors 37 and 39 best seen with reference to FIGS. 11 and 12.

Also seen in FIG. 13 are the buffer electronics 61 and 63 interposed between the pressure sensitive switches 27, 29, respectively, and the multiplexer 57. Also shown in FIG. 13 are integrator circuits 65 and 67 that receive signals from the fixed magnetic receivers 37, 39, respectively, integrate the signals and supply them to the multiplexer 57 for conveyance to the host computer 21 via the A/D converter 53 and the microcomputer 55.

FIG. 13 also shows the control sub-circuit for the transmitter 23 worn on the body of the user 1 as best seen in FIGS. 1-12. In particular, a conductor 71 emanates from the microcomputer 55 and provides control signals to control operation of the transmitter 23 via the D/A converter 73 and the multiplexer 75 in a manner well known to those skilled in the art.

Figure 14:
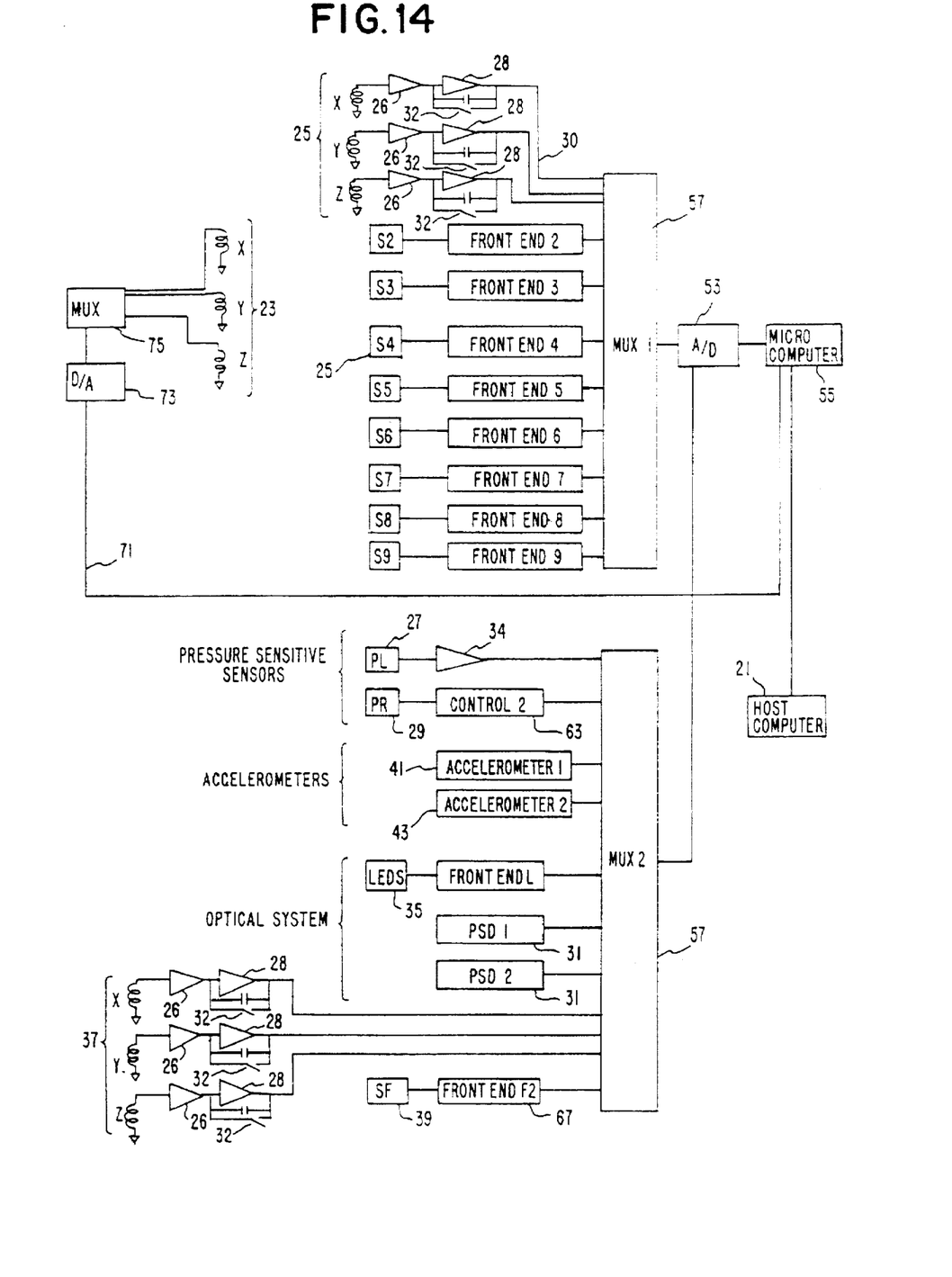
FIG. 14 shows a detailed block diagram of the electronics for all of the five embodiments of the present invention.

FIG. 14 shows further details in the form of a block diagram of all of the electronics in the inventive system. As seen in FIG. 14, each of the sensors 25 supplies signals to a preamplifier 26 that leads to an integrator 28 that supplies signals to the multiplexer 51 via an electrical conductor 30. A reset switch 32 allows resetting of each integrator 28 after each integration. The switches 32 may be suitably operated by the microcomputer 55.

The pressure sensitive switches 27, 29 are interconnected to the multiplexer 51 via preamplifiers 34. The fixed magnetic sensors 37, 39 interconnect to the multiplexer 51 via additional preamplifiers 26, integrators 28, and conductors 30. Reset switches 32 are also suitably provided.

Figure 15:
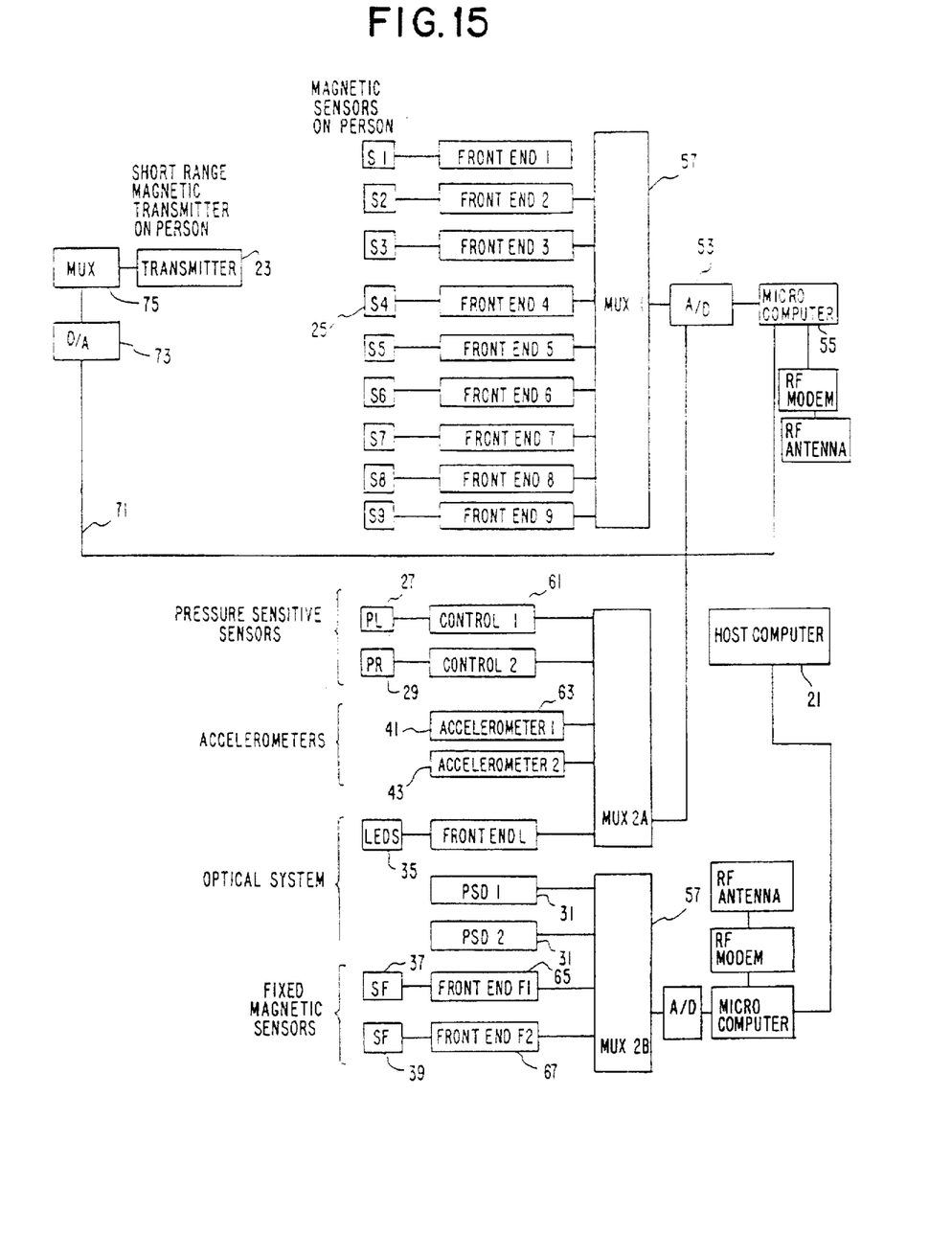
FIG. 15 shows a block diagram of a wireless system of all of the five embodiments of the present invention combined together.

FIG. 15 shows a schematic representation of the inventive system including wireless interconnection between fixed and moving portions thereof. As should be understood by those skilled in the art, wireless data transfer requires, for example, a spread spectrum radio modem transmitter/receiver. Such technology is well known to those skilled in the art.

In the embodiments of the present invention, nine sensors 25 are depicted. This depiction is considered merely exemplary and more or fewer sensors may be employed depending upon the particular application, that is, the type of motion to be measured. Of course, the inventive system may suitably be employed to keep track of the motions of a plurality of people merely by placing one transmitter and appropriate sensors on each of the people whose motions are being monitored.

The inventive system described hereinabove can employ any desired magnetic field position and orientation measurement system and, if desired, can utilize either AC or DC magnetic fields. Where a plurality of people are being tracked, it may be advantageous to utilize an AC magnetic field system since diverse transmission frequencies can be employed for each person in order to prevent interference from one sub-system to another. Alternatively, if the system uses DC magnetic fields, one may employ a suitable time multiplexing technique to provide the necessary timing between transmissions and signal receiving to prevent interference between sub-systems. The use of a time multiplexing technique will result in slower updating of the system, due to the delay between sequential measurements.

The embodiment of FIGS. 7-8 includes the utilization of an optical position and orientation system to measure the position and orientation of one sensor relative to a fixed coordinate system. Of course, if desired, this optical system may be replaced with a diverse system such as one employing electromagnetic waves, acoustical waves, mechanical arms of any shape and for one, two or three axis motion, etc.

Concerning the embodiment illustrated in FIGS. 9-10, a fixed three-axis magnetic receiver is included in order to facilitate finding of the position and orientation of a transmitter placed on the user 1. As should be understood by those skilled in the art, any magnetic field system utilizing two or three-axis transmitters and two or three-axis receivers may be suitably employed as an alternative.

In the embodiment of the present invention illustrated with reference to FIGS. 11-12, two three-axis magnetic receivers are employed in order to find the position and orientation of a long range single axis transmitter placed on the user 1. As should be understood by those skilled in the art, this system may be replaced with a magnetic field system using a one-axis transmitter and any number of receivers such as one-axis receivers, two-axis receivers, three-axis receivers or any combination thereof.

Accordingly, an invention has been disclosed in terms of preferred embodiments thereof which fulfill each and every one of the objects of the present invention as set forth hereinabove and provide a new and useful magnetic motion tracker system of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A motion tracking system for tracking motions of an object, comprising:
   a) a transmitter mounted on an object, said transmitter including three orthogonal magnetic coils including a one-axis long range transmitter and a two-axis short range transmitter;
   b) at least one sensor mounted on said object spaced from said transmitter;
   c) a computer including control means for controlling operation of said transmitter; and
   d) said computer receiving signals from said sensor and, therefrom, calculating position and orientation of said sensor with respect to said transmitter.

2. A motion tracking system for tracking motions of an object, comprising:
   a) a transmitter mounted on an object, said object comprising a person having a head, arms, legs, feet and lower back;
   b) at least one sensor mounted on said object spaced from said transmitter, said sensor comprising a plurality of discrete sensors mounted on a person;
   c) a computer including control means for controlling operation of said transmitter;
   d) said computer receiving signals from said sensor and, therefrom, calculating position and orientation of said sensor with respect to said transmitter; and
   e) said system further including an on-off switch mounted under one foot of the person, said switch being closed when said one foot is engaging a ground surface, said switch being incorporated into a sub-circuit connected to said computer whereby status of said switch is sensed by the computer.

3. The system of claim 2, including one on-off switch mounted under each foot of a person and interconnected in parallel sub-circuits with said computer.

4. A motion tracking system for tracking motions of an object, comprising:
   a) a transmitter mounted on an object, said object comprising a person having a head, arms, legs, feet and lower back;
   b) at least one sensor mounted on said object spaced from said transmitter, said sensor comprising a plurality of discrete sensors mounted on a person;
   c) a computer including control means for controlling operation of said transmitter;
   d) said computer receiving signals from said sensor and, therefrom, calculating position and orientation of said sensor with respect to said transmitter; and
   e) at least one accelerometer mounted on each foot of a person and interconnected to said computer.

5. A motion tracking system for tracking motions of an object, comprising:
   a) a first transmitter mounted on an object;
   b) a first sensor mounted on said object spaced from said first transmitter;
   c) a computer including control means for controlling operation of said first transmitter;
   d) said computer receiving first signals from said first sensor and, therefrom, calculating position and orientation of said first sensor with respect to said transmitter; and
   e) a second sensor located in a fixed location, and a second transmitter mounted on the object, said computer including further control means for controlling operation of said second transmitter, said computer receiving second signals from said second transmitter and, therefrom, calculating position and orientation of said second transmitter with respect to said second sensor;
   f) wherein said second transmitter comprises a light source and said second sensor comprises a light sensitive receiver.

6. The system of claim 5, said light source comprising an infrared light source and said second sensor comprising an infrared light sensitive position sensing detector.

7. A motion tracking system for tracking motions of an object, comprising:
   a) a transmitter mounted on an object;
   b) a first sensor mounted on said object spaced from said transmitter;
   c) a computer including control means for controlling operation of said transmitter;
   d) said computer receiving signals from said first sensor and, therefrom, calculating position and orientation of said first sensor with respect to said transmitter; and
   e) a second sensor located in a fixed location spaced from said object, said computer receiving further signals from said second sensor responsive to activation of said transmitter and, therefrom, determining position and orientation of said object with respect to a fixed coordinate system defined by said second sensor.

8. The system of claim 1, further including a further sensor located in a fixed location spaced from said object, said computer receiving further signals from said further sensor responsive to activation of said one-axis long range transmitter and, therefrom, determining position and orientation of said object with respect to a fixed coordinate system defined about said further sensor.

9. The system of claim 8, said further sensor comprising two further sensors.

10. A method of tracking motions of a person having a head, arms, legs, feet and a lower back, including the steps of:
    a) mounting a transmitter on a person's lower back;
    b) mounting a sensor on any one of the head, arm or leg of the person;
    c) providing a computer connected to control operation of said transmitter and to receive signals from said sensor;
    d) activating said transmitter to transmit magnetic fields;
    e) receiving signals from said sensor;
    f) calculating position and orientation of said sensor with respect to said transmitter;
    g) providing two on-off switches;
    h) mounting one of said switches on each foot of the person;
    i) electrically connecting said switches to said computer; and
    j) monitoring said switches to determine when one foot or both feet are engaging a floor surface.

11. A method of tracking motions of a person having a head, arms, legs, feet and a lower back, including the steps of:
    a) mounting a transmitter that transmits magnetic fields on a person's lower back;
    b) mounting a sensor on any one of the head, arm or leg of the person;
    c) providing a computer connected to control operation of said transmitter and to receive signals from said sensor;
    d) activating said transmitter to transmit magnetic fields;
    e) receiving signals from said sensor;
    f) calculating position and orientation of said sensor with respect to said transmitter;
    g) providing a further sensor;
    h) locating said further sensor in a fixed location spaced from said person;
    i) providing a further source and mounting said further source on the person;
    j) connecting said further source and further sensor to said computer;
    k) activating said further source;
    l) said further sensor receiving waves from said further transmitter;
    m) sending further signals from said further sensor to said computer; and
    n) calculating position and orientation of said person with respect to a fixed coordinate system defined by location of said further sensor.

12. The method of claim 11, wherein said further source comprises an infrared light source.

13. The method of claim 11, wherein said further sensor comprises at least one position sensing device.

14. A method of tracking motions of a person having a head, arms, legs, feet and a lower back, including the steps of:
    a) mounting a transmitter on a person's lower back;
    b) mounting a sensor on any one of the head, arm or leg of the person;

c) providing a computer connected to control operation of said transmitter and to receive signals from said sensor;

d) activating said transmitter to transmit magnetic fields;

e) receiving signals from said sensor;

f) calculating position and orientation of said sensor with respect to said transmitter; and g) providing a further sensor located in a fixed location with respect to said person.

15. A method of tracking motions of a person having a head, arms, legs, feet and a lower back, including the steps of:

a) mounting a transmitter on a person's lower back;

b) mounting a sensor on any one of the head, arm or leg of the person;

c) providing a computer connected to control operation of said transmitter and to receive signals from said sensor;

d) activating said transmitter to transmit magnetic fields;

e) receiving signals from said sensor;

f) calculating position and orientation of said sensor with respect to said transmitter; and g) providing two further sensors located in fixed locations with respect to said person.

16. The method of claim 15, further including the step of providing said transmitter with three mutually orthogonal coils which comprise a one-axis long range transmitter and a two-axis short range transmitter.

17. A method of tracking motions of a person having a head, arms, legs, feet and a lower back, including the steps of:

a) mounting a transmitter on a person's lower back;

b) mounting a sensor on any one of the head, arm or leg of the person;

c) providing a computer connected to control operation of said transmitter and to receive signals from said sensor;

d) activating said transmitter to transmit magnetic fields;

e) receiving signals from said sensor;

f) calculating position and orientation of said sensor with respect to said transmitter; and g) calculating motions of the person from calculations of sequential positions and orientations of said sensor with respect to said transmitter.

18. The method of claim 17, further including the step of mounting a sensor on each of said arm, said leg and said head.

19. The method of claim 17, further including the step of providing said transmitter with three mutually orthogonal magnetic coils.

20. The method of claim 19, further including the step of providing a plurality of sensors, each of which comprises three mutually orthogonal coils.

21. A motion tracking system for tracking motions of an object, comprising:

a) a transmitter mounted on an object;

b) at least one sensor mounted on said object spaced from said transmitter;

c) a computer including control means for controlling operation of said transmitter;

d) said computer receiving signals from said sensor and, therefrom, calculating position and orientation of said sensor with respect to said transmitter;

e) said computer receiving sequential signals from said sensor related to sequential positions and orientations of said sensor with respect to said transmitter and, therefrom, calculating motions of said object.

22. The system of claim 21, wherein said sensor is mounted on said object at a first location thereon movable with respect to a second location thereon where said transmitter is located, said computer further translating said position and orientation of said sensor into motion of said object.

23. The system of claim 21, wherein said sensor comprises a plurality of discrete sensors mounted at spaced locations on said object.

24. The system of claim 21, wherein said transmitter includes three mutually orthogonal magnetic coils.

25. The system of claim 24, wherein said sensor comprises three mutually orthogonal coils.

26. The system of claim 25, wherein said sensor comprises a plurality of discrete sensors mounted at spaced locations on said object.

27. The system of claim 21, wherein said object comprises a person having a head, arms, legs, feet and lower back, said sensor comprising a plurality of discrete sensors mounted on a person.

28. The system of claim 27, wherein said plurality of discrete sensors includes a first sensor mounted on a person's head, a second sensor mounted on one of the person's arms, and a third sensor mounted on one of the person's legs.

29. The system of claim 28, wherein said transmitter is mounted on a person's lower back.

30. A motion tracking system for tracking motions of an object, comprising:

a) a transmitter mounted on an object;

b) at least one sensor mounted on said object spaced from said transmitter;

c) a computer including control means for controlling operation of said transmitter;

d) said computer receiving signals from said sensor and, therefrom, calculating position and orientation of said sensor with respect to said transmitter;

e) a further sensor located in a fixed location separate from said object;

f) a further source mounted on said transmitter on said object;

g) said computer receiving further signals from said further sensor and, therefrom, calculating position and orientation of said further source with respect to said further sensor;

h) said computer further being programmed to determine position and orientation of said object with respect to a fixed coordinate system defined about said further sensor.

* * * * *